United States Patent
Bevis

(10) Patent No.: US 7,847,937 B1
(45) Date of Patent: Dec. 7, 2010

(54) OPTICAL MEASURMENT SYSTEMS AND METHODS

(75) Inventor: Christopher F. Bevis, Los Gatos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 774 days.

(21) Appl. No.: 11/696,612

(22) Filed: Apr. 4, 2007

(51) Int. Cl.
*G01J 4/00* (2006.01)

(52) U.S. Cl. .................. 356/369; 250/216; 250/226; 356/225; 356/364; 356/445

(58) Field of Classification Search ......... 250/216–226; 356/225, 364, 369, 234, 445, 381
See application file for complete search history.

(56) References Cited

U.S. PATENT DOCUMENTS

| | | | |
|---|---|---|---|
| 6,597,446 B2 * | 7/2003 | Klooster et al. ........ 250/559.45 |
| 7,239,392 B2 * | 7/2007 | Chism, II ................. 356/369 |
| 7,369,234 B2 * | 5/2008 | Beaglehole .............. 356/369 |
| 7,505,154 B2 * | 3/2009 | Maris ....................... 356/630 |

* cited by examiner

*Primary Examiner*—Gregory J Toatley
*Assistant Examiner*—Iyabo S Alli
(74) *Attorney, Agent, or Firm*—Joshua D. Isenberg; JDI Patent

(57) ABSTRACT

An optical measurement system includes a rotating element ellipsometer comprising a radiant source and a rotating optical element coupled to the radian source, an optical system to provide a modulated pump beam, a detection system optically coupled to the ellipsometer and a signal analyzer. The rotating element ellipsometer is configured to deliver a probe beam to a measurement spot on a sample and to measure one or more ellipsometric parameters of the sample at one or more discrete wavelengths or wavelength ranges, or a plurality of wavelengths across a wavelength range. Methods for determining sample characteristics from radiation scattered, reflected, diffracted or otherwise emitted from a sample surface using the optical measurement systems are also disclosed.

58 Claims, 4 Drawing Sheets

OPTICAL MEASURMENT SYSTEMS AND METHODS

FIELD OF THE INVENTION

This invention generally relates optical measurement systems and methods and more particularly to systems and methods for determining sample characteristics from radiation scattered, reflected, diffracted or otherwise emitted from a sample surface.

BACKGROUND OF THE INVENTION

Ellipsometry is currently used for the measurement of film thickness, dielectric function and composition. Ellipsometry is not sufficiently sensitive to certain electrical properties of materials such as band structure, mobility, trapped charge, etc. Similarly, modulated reflectance (e.g., photoreflectance, electroreflectance, etc.) are able to measure some of these properties but are often not sensitive enough.

It is within this context that embodiments of the present invention arise.

BRIEF DESCRIPTION OF THE DRAWINGS

Objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Because conventional spectrometer designs limit the sampling rate, previous attempts to use ellipsometry as a detection mechanism have been limited to single wavelength operation and polarization modulated ellipsometry makes more sense in that case. Certain embodiments of the present invention, by contrast, utilize a novel spectrometer, which enables rotating element spectroscopic detection in conjunction with extraction of a pump-modulation-synchronized signal on a per-pixel basis over a broad wavelength range.

Figure 1:
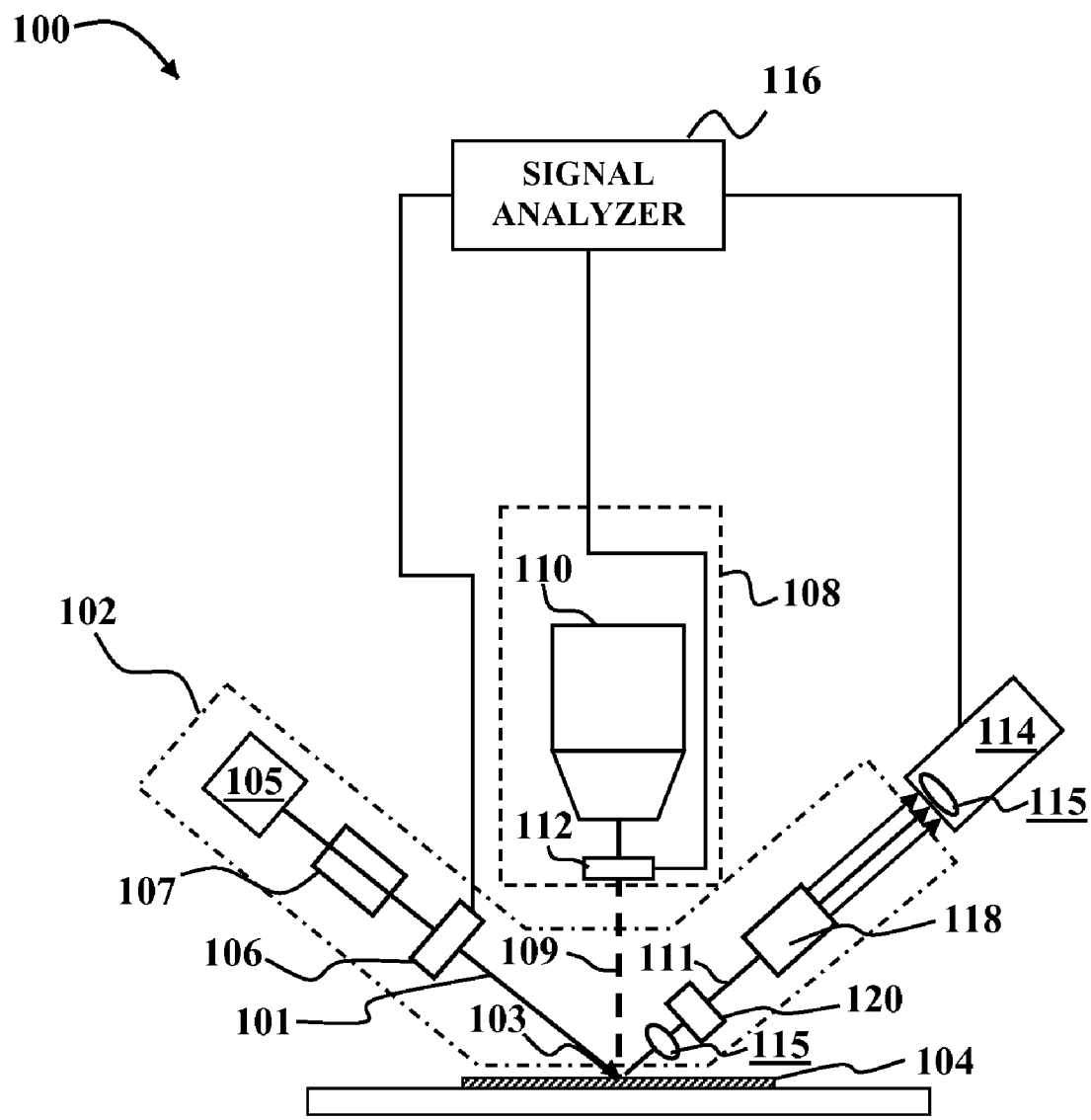
FIG. 1 is a schematic diagram of an optical measurement system according to an embodiment of the present invention.

FIG. 1 depicts an example of an optical measurement system 100 according to an embodiment of the present invention. The system 100 generally includes a rotating element ellipsometer 102 that is configured to deliver a probe beam 101 to a measurement spot 103 on a sample 104 and to measure one or more ellipsometric parameters of the sample 104 at one or more discrete wavelengths or wavelength ranges or over a range of wavelengths or for a plurality of wavelengths across a wavelength range. By way of example, the ellipsometer 102 may include a probe beam radiation source 105 and appropriate optical elements 107 for delivering the probe beam 101 to the measurement spot 103. The relevant wavelength range for the probe beam 101 varies from material to material depending on the band structure. By way of example, for Silicon, the relevant wavelength range is between about 350 nm and about 375 nm for the direct gap and about 1.0 micron to about 1.2 microns for the indirect gap.

The ellipsometer 102 includes a rotating optical element 106 that is configured to modulate a polarization of the probe beam. By way of example, the rotating optical element may be a polarizer, e.g., Nichol prism, or the like in a rotating mount that rotates about an axis parallel to an optical axis of the probe beam 101. Rotation of the optical element 106 modulates the polarization of the probe beam 101. The use of rotating element 106 to modulate the polarization allows for lower frequency modulation of the polarization, e.g. at modulation frequencies ranging from about 1-5 Hz up to about 60 Hz.

The ellipsometer 102 may further include an analyzer element 120 that selects a polarization of signal radiation 111 that is reflected, diffracted, scattered or otherwise emitted from the measurement spot 103 on the sample 104 as a result of interaction between the sample material and the probe beam 101. Additional optical components, e.g., lenses, mirrors, compensator plates, filters and the like, optically couple the signal radiation 111 (or a portion thereof) to a detection system 114, which may be part of the ellipsometer 102 or separate from it.

In embodiments of the present invention, the system 100 includes an optical system 108 is configured to provide a modulated pump beam 109 coincident or near to the measurement spot 103. By way of example, the optical system 108 may include a light source 110 and an optical modulator 112. The light source 110 may include a broadband source, such as a lamp, or a narrow band source, such as a laser. The modulator 112 varies the intensity of the pump beam 109 in a repetitive fashion. There modulator 112 may be implemented in a number of different ways. For example, light from the source 110 may pass through a rotating "chopper" wheel having a slot or sector-shaped opening. The rotation frequency of the chopper wheel determines the modulation frequency and the size and shape of the opening may be adjusted to vary the duty cycle of the pump beam modulation. The modulator 112 may alternatively include an acousto-optic or electro-optic element driven by a signal generator. In some embodiments, the modulator 112 may modulate the source 110 directly. For example, in the case of a laser, the modulator may modulate a source of pumping radiation applied to a gain medium that produces the pump beam 109. The optical system 108 may be configured to project the pump beam 109 onto the sample 104 in such a manner as to provide a substantially repetitive, spatially varying illumination on the sample surface. For example, projecting a repetitive pattern with the pump beam may create the equivalent of a diffraction grating on the sample, which may result in increased sensitivity in some cases.

In some embodiments of the invention, a synchronization signal generator may be coupled to the rotating element 106. The synchronization signal generator may be configured to generate a synchronization signal that depends upon rotation (e.g., frequency, phase, duty cycle, etc.) of the rotating element 106. The modulator 112 may be adapted to modulate the pump beam in response to synchronization signal. As a result, modulation of the pump beam may be synchronized to the rotation of the rotating element. As used herein, the term synchronized refers to a known or predictable relationship between a cycle of the pump modulation and a cycle of the rotation of the rotating element. Synchronization of the pump beam modulation and polarization rotation allows more accurate demodulation, especially if the separation between the two frequencies is not as large as might be desired.

As discussed above, the detection system 114 is optically coupled to the ellipsometer 102. By way of example, the ellipsometer 102 and/or detection system 114 may include optical components 115 that collect light scattered from or otherwise generated at the measurement spot 103 on the sample 104. The detection system 114 is configured to measure standard ellipsometric signals and/or signals due to effects of the modulated pump beam on one or more sample properties. A signal analyzer 116 is coupled to the detection system 114. The signal analyzer 116 is configured to extract one or more properties of the sample 104 from the standard ellipsometric signals, the parameters derived from the signals due to effects of the modulated pump beam, or both. By way of example, and without limitation, the signal analyzer may be implemented by code instructions running on a suitable processor. The signal analyzer may be implemented in hardware, in software or some combination of hardware and software.

Examples of properties that can be derived from standard ellipsometric parameters include, but are not limited to film thicknesses and dielectric function, substrate dielectric function, and, by inference, film stoichiometry. Examples of properties that can be derived from the signal due to modulation of the pump beam include, but are not limited to band structure, band gap, mobility, density of states, strain, dopant concentration and profile, and the like.

The optical system 108 may be configured to vary a wavelength of the pump beam 109 over one or more wavelength ranges. In general, the wavelength range of the pump beam 109 is sufficient to excite interactions between the probe beam 101 and the sample 104 over a wavelength range of interest. The wavelength range generally depends on the nature of the sample and the interactions. By wave of example, a useful wavelength range involves probe beam wavelengths ranging from about 150 nm to about 800 nm. To provide the pump beam with a corresponding range of wavelengths, the light source 110 may include a continuum pump light source and a variable filter or monochromator configured to select a particular wavelength or wavelength range for the pump beam 109 from among a range of wavelengths. Alternatively, the light source 110 may be otherwise configured to produce a wavelength-tunable pump beam. For example, the pump light source 110 may include a tunable laser. Examples of suitable tunable lasers include Vibrant model lasers available from Opotek, Inc. of Carlsbad, Calif. Further information about such lasers may be found on the Internet at http://www.opotek.com/vibrant.htm.

The optical system 108 may optionally include a polarization controller configured to control a polarization of the pump beam. The polarization controller may be configured to substantially linearly polarize or circularly polarize the pump beam.

In certain embodiments of the invention, the optical system 108 may be configured such that a wavelength of the pump beam can be selected from among a set of discrete wavelength choices. By way of example, such a configuration may be implemented by using a light source 110 having a lamp that produces a spectrum characterized by peaks at distinct wavelengths and a monochomator to select a particular peak for the pump beam 109. Alternatively, the light source 110 may include a broad spectrum lamp and a selectable set of wavelength filters coupled between the lamp and the sample 104. Furthermore, the light source 110 may include multiple lasers that may be selectively coupled to the measurement spot. Each laser may produce a different wavelength of pump radiation.

In a preferred embodiment, the optical system 108 is configured such that the pump beam 109 is characterized by photon energies near to or greater than an E1 transition of silicon. In particular, the vacuum wavelength for photons in the pump beam may be less than about 360 nanometers. This is a considerably shorter that the roughly 1.1 micron wavelength of the more commonly used E2 transition.

Pump beam modulation has not previously been used in rotating element ellipsometry. In the prior art, the polarization of the probe beam has been implemented using an electro-optic polarization rotator, such as a Pockels cell. The use of the rotating element 106 in the ellipsometer 102 allows for sensitivity over a broad wavelength range, e.g., from about 150 nanometers (nm) to about 800 nm. With electro-optic polarization rotation, by contrast, it is relatively difficult to get good data except over a very narrow wavelength range, e.g., only 30 to 40 nanometers wide. Also systems that use electro-optic polarization rotation tend to be limited in sensitivity over different sample types. In certain embodiments of the invention, the modulator 112 may be configured to modulate the pump beam 109 at a modulation frequency that is different than a rotation frequency of the rotating optical element 106.

In certain embodiments of the invention it may be desirable to separate the frequencies of the ellipsometer element rotation from the pump modulation frequency. To facilitate this, the modulation frequency may be either higher or lower than the rotation frequency. Considerable advantage may be obtained by modulating the pump at a much higher frequency than the ellipsometer, e.g., about 10 times higher or greater. The rapid modulation of the pump may allow for integration of the signal (or signals) detected by the detection system 114 over a cycle of rotation of the rotating element 106. This allows for greater sensitivity over a broader wavelength range without sacrificing precision or accuracy.

The optical system 108 may be configured to vary a modulation frequency of the pump beam 109 and determine a dependence of modulation intensity and phase on modulation frequency. The optical system 108 may also be configured to vary a duty cycle of the modulation of the pump beam and determine a dependence of the modulation signal on the duty cycle. By way of example, the modulator 112 may generate a reference signal that is synchronized to the modulation of the pump beam 109. The reference signal has a frequency that is the same as the modulation frequency or dependent on the modulation frequency in some known way. The duty cycle and phase of the reference signal may be the same as the duty cycle and phase of the pump beam modulation or may be dependent on the pump beam modulation phase and duty in some known way. The reference signal may be coupled to the detection system 114 and/or signal analyzer 116. The detection system 114 and/or signal analyzer 116 may be configured to integrate a signal from the detection system over a fraction of a rotation cycle of the rotating optical element 106, e.g. between about one sixteenth and about one quarter of the rotation cycle. Integrating the signal in this fashion allows for sensitivity over a broader wavelength range (e.g., 150 nm to about 800 nm) with sacrificing precision or accuracy. By way of comparison, conventional pump modulated ellipsometry using, e.g., a Pockels cell for probe beam polarization modulation can only provide sensitivity over a wavelength range roughly 30 to 40 nanometers wide.

The ellipsometer 102 may include a spectrometer 118 configured to resolve the standard ellipsometric signals and the signals due to effects of the modulated pump beam 109 at each of a plurality of wavelengths. By way of example, the spectrometer 118 may be a dispersive spectrometer. Alternatively, the spectrometer 118 may be a Fourier transform spectrometer. Alternatively, the spectrometer 118 may include a monochromator or variable filter configured to sequentially select one or more of the plurality of wavelengths from the probe beam 109.

Figure 2:
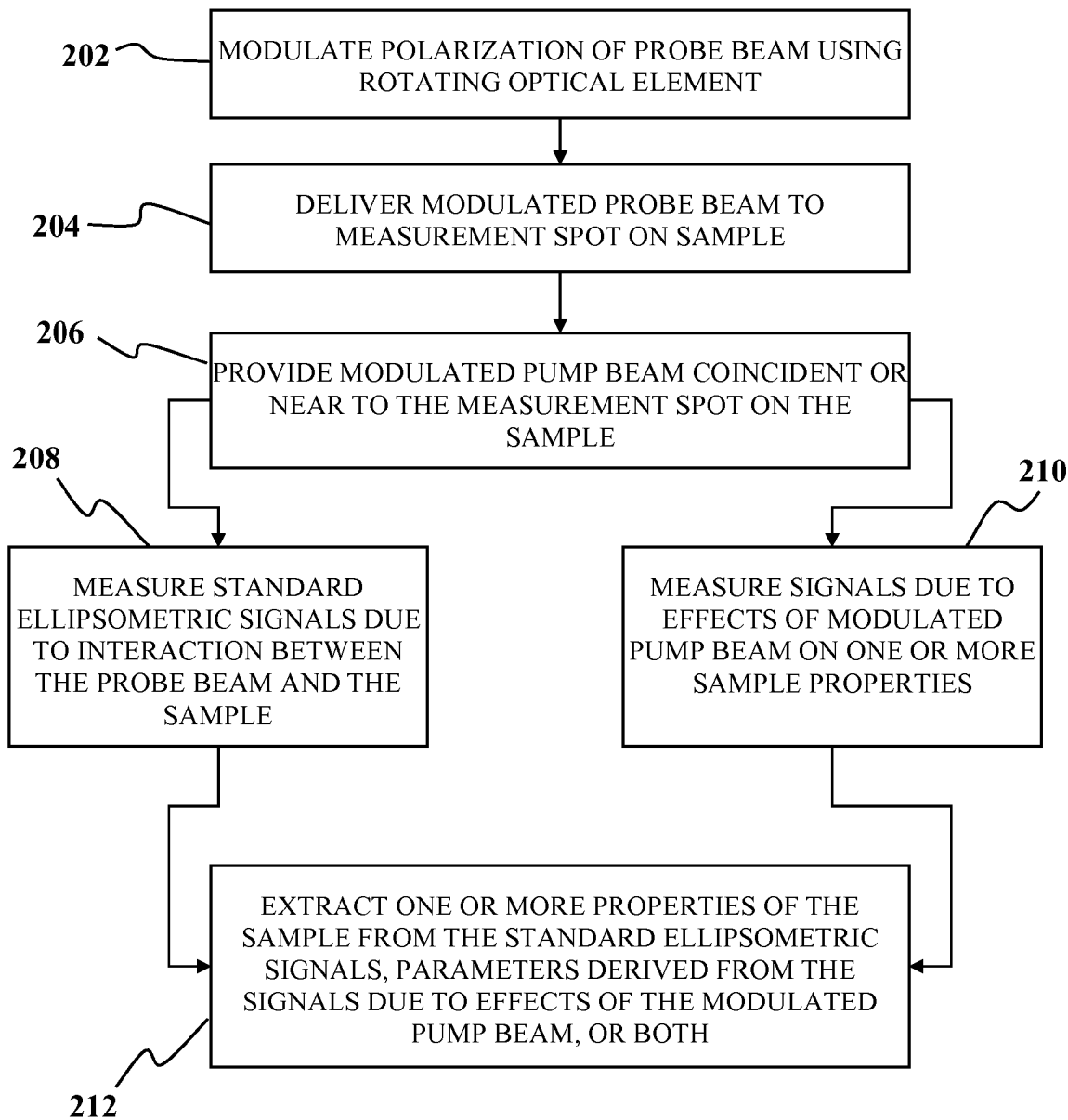
FIG. 2 is a flow diagram illustrating an optical measurement method according to an embodiment of the present invention.

According to an embodiment of the present invention an optical measurement method may be implemented using a system of the type shown in FIG. 1. As depicted in FIG. 2, the method 200 may proceed by modulating a polarization of a beam of radiation using the rotating optical element 106 to produce a polarization-modulated probe 101 beam as indicated at 202. The probe beam 101 is delivered to the measurement 103 spot on the sample 104 as indicated at 204. A modulated pump beam 109 is provided coincident or near to the measurement spot on the sample as indicated at 206. Standard ellipsometric signals due to interaction between the probe beam 101 and the sample 104 are measured as indicated at 208. In addition or as an alternative to these signals, other signals due to effects of the modulated pump beam 109 on one or more sample properties may also be measured as indicated at 210. One or more properties of the sample are then extracted from the standard ellipsometric signals, the parameters derived from the signals due to effects of the modulated pump beam, or both, as indicated at 212.

Standard Ellipsometry typically measures two of the four Stokes parameters, which are conventionally denoted by $\Psi$ and $\Delta$. The Stokes parameters are a set of values that describe the polarization state of electromagnetic radiation. The polarization state of the light incident upon the sample may be decomposed into an s and a p component (the s component is oscillating perpendicular to the plane of incidence and parallel to the sample surface, and the p component is oscillating parallel to the plane of incidence). The amplitudes of the s and p components, after reflection and normalized to their initial value, are denoted by $R_s$ and $R_p$, respectively. Ellipsometry measures $\rho$ the ratio of $R_s$ and $R_p$, which is described by the fundamental equation of ellipsometry:

$$\rho = \frac{R_p}{R_s} = \tan(\Psi)e^{i\Delta}$$

Thus, $\tan \Psi$ is the amplitude ratio upon reflection, and $\Delta$ is the phase shift.

Ellipsometry is in indirect method, i.e. in general the measured $\Psi$ and $\Delta$ cannot be converted directly into the optical constants of the sample. Normally, a model analysis must be performed to extract parameters of the sample. Such models may be implemented in software running on the signal analyzer. Direct inversion of $\Psi$ and $\Delta$ is possible in certain simple cases involving isotropic and homogeneous thick films. In other cases a layer model is established, which considers the optical constants (e.g., refractive index or dielectric function tensor) and thickness parameters of all individual layers of the sample including the correct layer sequence. Using an iterative procedure (least-squares minimization) unknown optical constants and/or thickness parameters are varied, and $\Psi$ and $\Delta$ values are calculated using the Fresnel equations. The calculated $\Psi$ and $\Delta$ values, which match the experimental data best, provide the optical constants and thickness parameters of the sample.

Figure 3A:
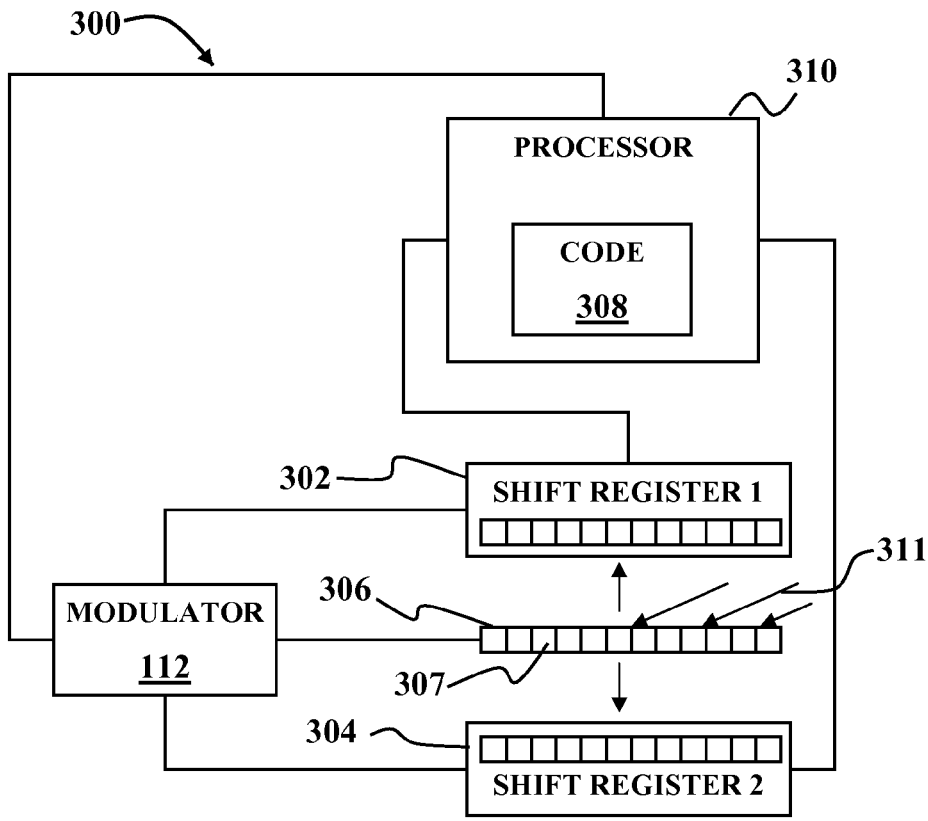
FIG. 3A is a schematic diagram illustrating an optical measurement system according to an alternative embodiments of the present invention.
Figure 3B:
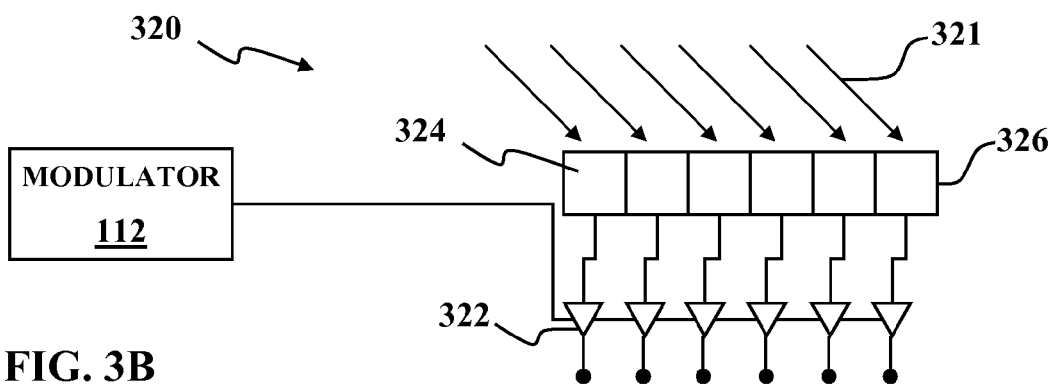
FIG. 3B is a schematic diagram illustrating an optical measurement system according to another alternative embodiments of the present invention.

In certain embodiments of the invention, the detection system 114 may be configured to receive signal radiation from the measurement spot 104 at a plurality of detector elements. Each detector element may be configured to generate a pixel signal in response to a corresponding part of the signal radiation, thereby generating a plurality of pixel signals. FIGS. 3A-3B depict two examples, among others, of possible configurations of the detection system 114 for such embodiments. Where pump beam modulation is used, the signal analyzer 116 may be configured to extract from each pixel signal a component that is synchronized to modulation of the pump beam 109. Each detector element receives light of a different energy or wavelength from the sample. Therefore, each pixel signal may correspond to pump-modulation-synchronized signal radiation 111 from the measurement spot 104 for a different part of the spectrum of the signal radiation, e.g., a different energy or wavelength.

There are a number of different ways of configuring the signal analyzer to extract a pump-modulation-synchronized signal on a per-pixel basis. By way of example, as shown in FIG. 3A a signal analyzer apparatus 300 that may be used as the signal analyzer 116 of FIG. 1 may include first and second transfer registers 302, 304 coupled to a detector element array 306 made up of a plurality of detector elements 307, each of which produces a different pixel signal in response to radiation 311 incident on the detector element. The transfer registers and detector element array 306 may respond to execution of coded instructions 308 on a processor 310. The detector element array 306 and processor are configured to accumulate a first set of pixel signals in the first transfer register 302 but not the second transfer register 304 over a first portion of a modulation cycle and accumulate a second set pixel signals in the second transfer 304 register but not the first transfer register 302 over a second portion of the modulation cycle. The shift registers 302, 304 and/or detector array 306 and/or processor 310 may use a modulation signal from the modulator 112 to determine the relevant periods of time over which to accumulate pixel signals in the first and second transfer registers. The processor 310 may be configured (e.g., by appropriate coded instructions) to perform a comparison operation between the first and second sets of pixel signals to extract a set of per-pixel signal components that are synchronized to the modulation of the source radiation by the modulator. By way of example, the comparison operation may include a subtraction, ratio calculation, statistical analysis, and the like.

In an alternative embodiment, shown in FIG. 3B the signal analyzer 116 may be implemented as an apparatus 320 that includes a plurality of lock-in amplifiers 322. Each lock-in amplifier 322 receives a pixel signal from a corresponding detector element 324 in a detector 326. Each detector element is preferably a non-charge-coupled device. Each detector element 324 produces a signal that is related to the intensity of radiation 321 incident on the detector element. By way of example, each detector element 324 may be a photodiode. Each lock-in amplifier 322 also receives the reference signal from the modulator 112.

The signal analyzer apparatus 300 or lock-in amplifiers 322 may be configured to integrate each pixel signal over a fraction of a rotation cycle of the rotating optical element.

Apparatus of the type shown in FIG. 1 and FIGS. 3A-3B or other similarly configured apparatus may be used to implement an optical measurement method according to an alternative embodiment of the invention. As shown in the flow diagram of FIG. 4, such a method 400 may proceed as follows. Source radiation is modulated as indicated at 402. By way of example, the source radiation being modulated may be pump radiation or radiation for a probe beam, e.g., as described above. The source radiation is delivered to a measurement spot on a sample as indicated at 404. The modulation of the source radiation may involve modulation of the amplitude and/or phase of the source radiation and/or modulation of the polarization of the source radiation, e.g., using a rotating optical element. The source radiation may be delivered using conventional optical components, e.g., lenses, mirrors, and the like disposed along an optical path between an illumination source that generates the source radiation and the measurement spot on the sample.

A plurality of detector elements receive signal radiation from the measurement spot as indicated at 406. As used herein, signal radiation generally refers to radiation that is produced as a result of interaction involving the source radiation and the sample at the measurement spot. Examples of signal radiation include radiation that is reflected, diffracted, scattered or otherwise emitted from the measurement spot. The signal radiation may include (but need not necessarily be) a portion of the source radiation that is reflected, diffracted or scattered from the sample. Each detector element generates a pixel signal in response to a corresponding part of the signal radiation as indicated at 408, thereby generating a plurality of pixel signals. A 410, a component that is synchronized to the modulation of the source radiation is extracted from each pixel signal. By way of example, and without limitation, the modulation-synchronized pixel signal components may be extracted as described above with respect to FIG. 3A and FIG. 3B.

Figure 4:
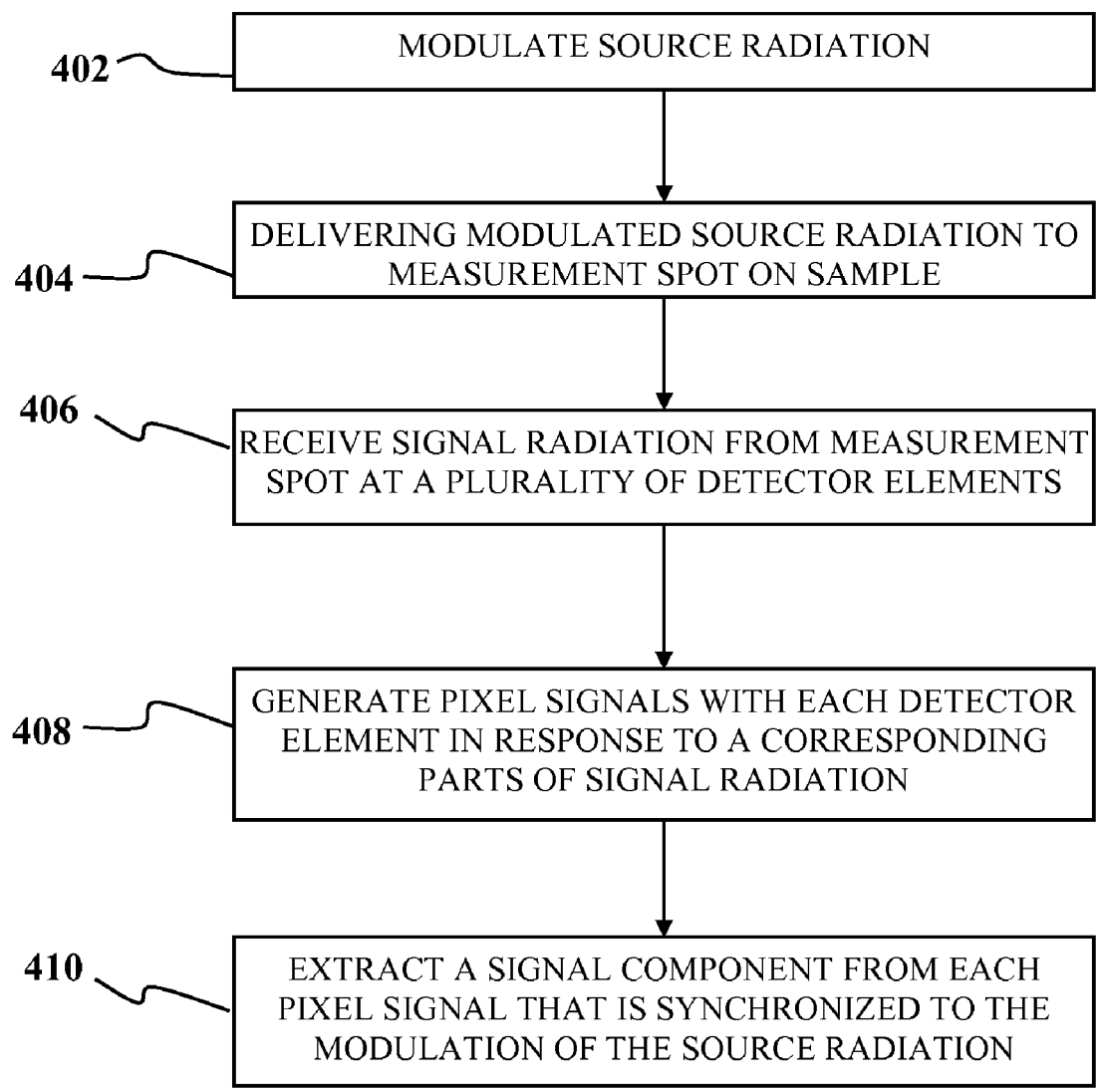
FIG. 4 is a flow diagram an optical measurement method according to an alternative embodiment of the present invention.

Per-pixel modulation synchronized signal components generated as described with respect to FIGS. 3A-3B and FIG. 4 may be used in conjunction with a measurement system of the type shown in FIG. 1 or variations thereon. For example, the probe beam source 105, pump radiation source 110 and detection system 114 may be configured as a pump modulated scatterometer. As used herein, the term scatterometer refers to an instrument used to determine the absolute or relative levels of optical scattering from surfaces. Alternatively, the probe beam source 105, pump radiation source 110 and detection system 114 may be configured as a pump modulated reflectometer. As used herein the term reflectometer refers to an instrument that measures the reflectance of a surface. A pump modulated reflectometer is similar to an ellipsometer, such as the one shown in FIG. 1. The probe beam of a reflectometer is generally not polarization modulated as in an ellipsometer. Thus a reflectometer does not require the polarization rotating optical element 106 and analyzer 120.

Pump-modulated reflectometers may be based on photo reflectance spectrometry, which may be used to non-destructively determine electron mobility characteristics of semiconductor materials. This technique may use a white light source with a monochromator to direct a probe beam onto a surface of a sample, such as a semiconductor wafer. The probe beam may be scanned through a full frequency range with the monochomator. A photo sensor measures the intensity of the reflected light from the probe beam. A laser beam may be used with an optical chopper to provide a modulated pump beam to the measurement spot. The pump beam injects electron-hole pairs into the material. The presence of these electron-hole pairs changes the reflectance characteristics of the wafer. These changes are detected by the photo sensor.

Each different wavelength (or energy) of reflected light may be received at a different detector element to produce multiple pixel signals. The pixel signals of the different detector elements thus provide information on the effect of the pump modulation at different wavelengths or energies of incident probe beam radiation.

There are well defined and highly complex theoretical equations defining the relationship between the change in reflectance ($\Delta R$) and the specific characteristics of the sample being measured. Embedded software line fitting algorithms may be used to extract the required parameter values automatically. Examples of parameters that can be extracted are bandgap energy for Gallium Nitride high brightness light-emitting diodes (HBLEDs) or Lattice Strain level in strained substrates, such as Silicon wafers. These parameter values may be plotted for multiple measurement points on the sample to generate a wafer map. This is used in the production environment for statistical process control purposes.

The presence of electron-hole pairs into the sample due the pump beam may also affect the polarization of light reflected by the sample. Therefore, measurement of such polarization changes, e.g., through pump-modulated ellipsometry, e.g., using a system of the type shown in FIG. 1, can provide information about parameters of the substrate. Examples of properties that can be derived from the signal due to modulation of the pump beam include, but are not limited to band structure, band gap, mobility, density of states, strain, dopant concentration and profile, and the like.

Embodiments of the present invention provide increased sensitivity, accuracy and decorrelation of parameters as well as reduced effects of undesirable process variation.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. An optical measurement system comprising:
   a rotating element ellipsometer configured to deliver a probe beam to a measurement spot on a sample and to measure one or more ellipsometric parameters of the sample at one or more discrete wavelengths or wavelength ranges, wherein the rotating element ellipsometer includes a rotating optical element that is configured to modulate a polarization of the probe beam;
   an optical system configured to provide a modulated pump beam coincident or near to the measurement spot on the sample;
   a detection system optically coupled to the ellipsometer, wherein the detection system is configured to measure standard ellipsometric signals and/or signals due to effects of the modulated pump beam on one or more sample properties; and
   a signal analyzer configured to extract one or more properties of the sample from the standard ellipsometric signals, the parameters derived from the signals due to effects of the modulated pump beam, or both
   wherein the detection system is configured to receive signal radiation that is produced as a result of interaction involving the probe beam and the sample at the measurement spot at a plurality of detector elements, wherein each detector element is a non-charge-coupled device configured to generate a pixel signal in response to a different corresponding part of a spectrum of the signal radiation, whereby the detection system generates a plurality of pixel signals, wherein the signal analyzer includes a plurality of lock-in amplifiers, wherein each lock-in amplifier is coupled to receive a pixel signal from a corresponding detector element and wherein each lock-in amplifier is configured to receive the reference signal from the modulator.

2. The system of claim 1, wherein the optical system is configured to vary a wavelength of the pump beam over one or more wavelength ranges.

3. The system of claim 2, wherein the optical system includes a continuum pump light source and a variable filter or monochromator configured to select a wavelength.

4. The system of claim 2, wherein the optical system includes a pump light source configured to produce a wavelength-tunable pump beam.

5. The system of claim 4, wherein the pump light source includes a tunable laser.

6. The system of claim 1, wherein the optical system is configured such that the pump beam is characterized by photon energies near to or greater than an E1 transition of silicon.

7. The system of claim 1, wherein the probe beam is characterized by wavelengths in the range between about 150 nm and about 800 nm.

8. The system of claim 1, wherein the optical system is configured to select a wavelength of the pump beam from among a set of discrete wavelength choices.

9. The system of claim 1, wherein the optical system is configured to modulate the pump beam at a modulation frequency that is different than a rotation frequency of the rotating optical element.

10. The system of claim 9, wherein the modulation frequency of the pump beam is greater than the rotation frequency of the rotating optical element.

11. The system of claim 10, wherein the modulation frequency of the pump beam is about 10 or more times the rotation frequency of the rotating optical element.

12. The system of claim 1, wherein the optical system is configured to vary a modulation frequency of the pump beam and determine a dependence of modulation intensity and phase on modulation frequency.

13. The system of claim 1, wherein the optical system is configured to vary a duty cycle of the modulation of the pump beam and determine a dependence of the modulation signal on the duty cycle.

14. The system of claim 1, wherein the optical system includes a polarization controller configured to control a polarization of the pump beam.

15. The system of claim 14, wherein the polarization controller is configured to substantially linearly polarize the pump beam.

16. The system of claim 14, wherein the polarization controller is configured to substantially circularly polarize the pump beam.

17. The system of claim 1, wherein the optical system is configured to project the pump beam onto the sample in such a manner as to provide a substantially repetitive, spatially varying illumination on the sample surface.

18. The system of claim 1, wherein the signal analyzer is configured to extract from each pixel signal a component that is synchronized to modulation of the pump beam.

19. The system of claim 1, wherein the signal analyzer includes first and second transfer registers coupled to the detection system, wherein the detection system and signal analyzer are configured to accumulate a first set of pixel signals in the first transfer register but not the second transfer register over a first portion of a modulation cycle and accumulate a second set pixel signals in the second transfer register but not the first transfer register over a second portion of the modulation cycle, wherein the signal analyzer is configured to perform a comparison operation between the first and second sets of pixel signals to extract a set of components that are synchronized to the modulation of the source radiation by the modulator.

20. The system of claim 1, wherein the detection system and/or signal analyzer is configured to integrate each pixel signal over a fraction of a rotation cycle of the rotating optical element.

21. The system of claim 1, wherein the detection system and/or signal analyzer is configured to integrate each signal from the detection system over a fraction of a rotation cycle of the rotating optical element.

22. An optical measurement system comprising:
a modulator having a rotating element spectroscopic ellipsometer configured to deliver a probe beam to a measurement spot on a sample and to measure one or more ellipsometric parameters at a measurement spot on a sample for a plurality of wavelengths across a wavelength range, wherein the rotating element ellipsometer includes a rotating optical element that is configured to modulate a polarization of the probe beam;
an optical system configured to provide a modulated pump beam coincident or near to the measurement spot on the sample;
a detection system on the ellipsometer configured to measure standard ellipsometric signals and/or signals due to effects of the modulated pump beam on one or more sample properties; and
a signal analyzer configured to extract one or more properties of the sample from the standard ellipsometric signals, parameters derived from the signals due the effects of the modulated to pump beam, or both
wherein the detection system is configured to receive signal radiation that is produced as a result of interaction involving the probe beam and the sample at the measurement spot at a plurality of non-charge-coupled device detector elements, wherein each detector element is configured to generate a pixel signal in response to a different corresponding part of a spectrum of the signal radiation, whereby the detection system generates a plurality of pixel signals, wherein the signal analyzer includes a plurality of lock-in amplifiers, wherein each lock-in amplifier is coupled to receive a pixel signal from a corresponding detector element and wherein each lock-in amplifier is configured to receive the reference signal from the modulator.

23. The system of claim 22, wherein the ellipsometer includes a dispersive spectrometer configured to resolve the standard ellipsometric signals and the signals due to effects of the modulated pump beam at each of the plurality of wavelengths.

24. The system of claim 22, wherein the ellipsometer includes a Fourier transform spectrometer configured to resolve the standard ellipsometric signals and the signals due to effects of the modulated pump beam at each of the plurality of wavelengths.

25. The system of claim 22, wherein the ellipsometer includes a monochromator or variable filter configured to sequentially select one or more of the plurality of wavelengths from a probe beam that is optically coupled to the measurement spot.

26. The system of claim 22, wherein the optical system includes a pump light source configured to vary a wavelength of the pump beam over one or more wavelength ranges.

27. The system of claim 26, wherein the pump light source is a continuum source and the optical system includes a variable filter or monochromator configured to select the wavelength of the pump beam.

28. The system of claim 26, wherein the pump light source is configured to produce a wavelength-tunable pump beam.

29. The system of claim 28, wherein the pump light source is a tunable laser.

30. The system of claim 22, wherein the optical system is configured to select a wavelength of the pump beam from among a set of discrete wavelength choices.

31. The system of claim 22, further comprising a synchronization signal generator coupled to the rotating element, wherein the synchronization signal generator is configured to generate a synchronization signal that depends upon rotation of the rotating element, wherein the optical system includes a pump beam modulator adapted to modulate the pump beam in response to synchronization signal, whereby modulation of the pump beam is synchronized to the rotation of the rotating element.

32. The system of claim 22, wherein the optical system is configured to modulate the pump beam at a modulation frequency that is much lower than a rotation frequency of the rotating optical element.

33. The system of claim 22, wherein the optical system is configured to vary a modulation frequency of the pump beam and determine a dependence of modulation intensity and phase on modulation frequency.

34. The system of claim 22, in which the duty cycle of the modulation of the pump beam is varied and the dependence of the modulation signal on the duty cycle is determined.

35. The system of claim 22, wherein the optical system includes a polarization controller configured to control a polarization of the pump beam.

36. The system of claim 22, wherein the polarization controller is configured to substantially linearly polarize the pump beam.

37. The system of claim 36, wherein the polarization controller is configured to substantially circularly polarize the pump beam.

38. The system of claim 22, wherein the optical system is configured to project the pump beam onto the sample in such a manner as to provide a substantially repetitive, spatially varying illumination on the sample surface.

39. The system of claim 22, wherein the signal analyzer is configured to extract from each pixel signal a component that is synchronized to modulation of the pump beam.

40. The system of claim 22, wherein the signal analyzer includes first and second transfer registers coupled to the detection system, wherein the detection system and signal analyzer are configured to accumulate a first set of pixel signals in the first transfer register but not the second transfer register over a first portion of a modulation cycle and accumulate a second set pixel signals in the second transfer register but no the first transfer register over a second portion of the modulation cycle, wherein the signal analyzer is configured to perform a comparison operation between the first and second sets of pixel signals to extract a set of components that are synchronized to the modulation of the source radiation by the modulator.

41. The system of claim 22, wherein the detection system and/or signal analyzer is configured to integrate each pixel signal over a fraction of a rotation cycle of the rotating optical element.

42. The system of claim 22, wherein the detection system and/or signal analyzer is configured to integrate each signal from the detection system over a fraction of a rotation cycle of the rotating optical element.

43. An optical measurement system comprising:
a radiation source configured to deliver source radiation to a measurement spot on a sample;
a detection system configured to receive signal radiation that is produced as a result of interaction involving the source radiation and the sample at the measurement spot at a plurality of non-charge-coupled device detector elements, wherein each detector element is configured to generate a pixel signal in response to a different corresponding part of a spectrum of the signal radiation, whereby the detection system generates a plurality of pixel signals;
a signal analyzer coupled to the detection system;
a modulator coupled to the radiation source, the modulator being configured to modulate the source radiation and generate a reference signal that is synchronized to modulation of the source radiation by the modulator,
wherein the reference signal is coupled to the detection system and/or signal analyzer,
wherein the signal analyzer is configured to extract from each pixel signal a component that is synchronized to the modulation of the source radiation by the modulator, wherein the signal analyzer includes a plurality of lock-in amplifiers, wherein each lock-in amplifier is coupled to receive a pixel signal from a corresponding detector element and wherein each lock-in amplifier is configured to receive the reference signal from the modulator.

44. The system of claim 43, wherein the signal analyzer includes first and second transfer registers coupled to the detection system, wherein the detection system and signal analyzer are configured to accumulate a first set of pixel signals in the first transfer register but not the second transfer register over a first portion of a modulation cycle and accumulate a second set pixel signals in the second transfer register but no the first transfer register over a second portion of the modulation cycle, wherein the signal analyzer is configured to perform a comparison operation between the first and second sets of pixel signals to extract a set of components that are synchronized to the modulation of the source radiation by the modulator.

45. The system of claim 43, wherein the radiation source is a source of probe radiation, the system further comprising a pump beam source configured to deliver a beam of pump radiation to the measurement spot.

46. The system of claim 43, wherein the source of radiation is a source of pump radiation, whereby the modulator modulates the pump radiation, the system further comprising a probe beam source configured to deliver a beam of probe radiation to the measurement spot.

47. The system of claim 46, wherein the probe beam source, source of pump radiation and detection system are configured as a pump modulated scatterometer.

48. The system of claim 46, wherein the probe beam source, source of pump radiation and detection system are configured as a pump modulated reflectometer.

49. The system of claim 46, wherein the probe beam source, source of pump radiation and detection system are configured as a pump modulated ellipsometer.

50. The system of claim 49, further comprising a rotating optical element that is configured to modulate a polarization of the probe beam.

51. The system of claim 50, wherein the modulator is configured to modulate the pump beam at a modulation frequency that is different than a rotation frequency of the rotating optical element.

52. The system of claim 51, wherein the modulator is configured to modulate the pump beam at a modulation frequency that is higher than the rotation frequency of the rotating optical element.

53. The system of claim 52, wherein the modulation frequency of the pump beam is about 10 or more times the rotation frequency of the rotating optical element.

54. The system of claim 52, wherein the detection system and/or signal analyzer is configured to integrate each pixel signal over a fraction of a rotation cycle of the rotating optical element.

55. The system of claim 54, wherein the fraction is between about one sixteenth and about one quarter of the rotation cycle.

56. An optical measurement method comprising:
modulating a polarization of a beam of radiation using a modulator having rotating optical element to produce a modulated probe beam;
delivering the modulated probe beam to a measurement spot on a sample;
providing a modulated pump beam coincident or near to the measurement spot on the sample;
measuring standard ellipsometric signals due to interaction between the probe beam and the sample and/or signals due to effects of the modulated pump beam on one or more sample properties by receiving signal radiation that is produced as a result of interaction involving the probe beam and the sample at the measurement spot at a plurality of non-charge-coupled device detector elements, wherein each detector element is configured to generate a pixel signal in response to a different corresponding part of a spectrum of the signal radiation, whereby the detection system generates a plurality of pixel signals,
wherein the pixel signals are coupled to a corresponding plurality of lock-in amplifiers,
wherein each lock-in amplifier is coupled to receive a pixel signal from a corresponding detector element and wherein each lock-in amplifier is configured to receive the reference signal from the modulator; and
extracting one or more properties of the sample from the standard ellipsometric signals, the parameters derived from the signals due to effects of the modulated pump beam, or both.

57. An optical measurement method comprising:
modulating source radiation, with a modulator;
delivering the source radiation to a measurement spot on a sample;
receiving signal radiation that is produced as a result of interaction involving the source radiation and the sample at the measurement spot at a plurality of non-charge-coupled device detector elements, wherein each detector element is configured to generate a pixel signal in response to a different corresponding part of a spectrum of the signal radiation, whereby the detection system generates a plurality of pixel signals;
generating a pixel signal with each detector element in response to a different corresponding part of a spectrum of the signal radiation, thereby generating a plurality of pixel signals, wherein the pixel signals are coupled to a corresponding plurality of lock-in amplifiers, wherein each lock-in amplifier is coupled to receive a pixel signal from a corresponding detector element and wherein each lock-in amplifier is configured to receive the reference signal from the modulator;
extracting from each pixel signal a component that is synchronized to the modulation of the source radiation.

58. The system of claim 57, wherein extracting from each pixel signal a component that is synchronized to the modulation of the source radiation includes accumulating a first set of pixel signals in a first transfer register over a first portion of a modulation cycle, accumulating a second set pixel signals in a second transfer register over a second portion of the modulation cycle and performing a comparison operation between the first and second sets of pixel signals to extract a set of components that are synchronized to the modulation.

* * * * *